(12) United States Patent
Zhou et al.

(10) Patent No.: US 7,141,398 B2
(45) Date of Patent: Nov. 28, 2006

(54) METHODS FOR RECYCLING MRNA FOR LINEAR CRNA AMPLIFICATION

(75) Inventors: Mingjie Zhou, Kirkland, WA (US); Sven Duenwald, Lake Forest Park, WA (US); Mark Parrish, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 221 days.

(21) Appl. No.: 10/745,462

(22) Filed: Dec. 23, 2003

(65) Prior Publication Data

US 2004/0191814 A1   Sep. 30, 2004

Related U.S. Application Data

(60) Provisional application No. 60/437,246, filed on Dec. 30, 2002.

(51) Int. Cl.
    C12P 19/34   (2006.01)
    C12Q 1/68    (2006.01)
    C12N 9/00    (2006.01)
    C12N 9/96    (2006.01)

(52) U.S. Cl. .................. 435/91.5; 435/6; 435/91.2; 435/183; 435/188

(58) Field of Classification Search ............... 435/91.1, 435/91.2, 91.21, 91.5, 91.51, 188, 6
    See application file for complete search history.

(56) References Cited

U.S. PATENT DOCUMENTS

| | | | | |
|---|---|---|---|---|
| 5,244,797 | A * | 9/1993 | Kotewicz et al. ............ | 435/194 |
| 6,271,002 | B1 * | 8/2001 | Linsley et al. ............. | 435/91.1 |
| 6,518,019 | B1 * | 2/2003 | Gerard et al. ................. | 435/6 |
| 2002/0090618 | A1 * | 7/2002 | Smith et al. ................. | 435/6 |
| 2004/0067492 | A1 * | 4/2004 | Peng et al. ................... | 435/6 |

OTHER PUBLICATIONS

Mallet, F. et al. (1995) Continuous RT-PCR using AMV-RT and Taq DNA Polymerase: Characterization and comparison to uncoupled procedures. Biotechniques 18, 678-687.*

Qiu, Y. and Park, K. (2001) Environment-sensitive hydrogels for drug delivery. Advanced Drug Delivery Reviews 53, 321-339.*

Feil, H. et al. (1993) Effect of comonomer hydrophilicity and ionization on the lower critical solution temperature of N-Isopropylacrylamide copolymers. Macromolecules 26, 2496-2500.*

Carninci, P. et al. (1998) Thermostabilization and thermoactivation of thermolabile enzymes by trehalose and its application for the synthesis of full-length cDNA. Proc. Natl. Acad. Sci., USA 95, 520-524.*

Duggan, D.J., et al., "Expression Profiling Using cDNA Microarrays," *Nature Genetics Supplement* 21:10-14; Jan. 1999.

Lockhart, D.J., et al., "Expression Monitoring by Hybridization to High-Density Oligonucleotide Arrays," *Nature Biotechnology* 14:1675-1680, Dec. 1996.

McGall, G., et al., "Light-Directed Synthesis of High-Density Oligonucleotide Arrays Using Semiconductor Photoresists," *Proc. Natl. Acad. Sci. USA* 93:13555-13560, Nov. 1996.

Ramaswamy, S., and T.R. Golub, DNA Microarrays in Clinical Oncology,*Journal of Clinical Oncology* 20(7):1932-1941, Apr. 2002.

Schena, M., et al., "Quantitative Monitoring of Gene Expression Patterns With a Complementary DNA Microarray," *Science* 270:467-470, Oct. 20, 1995.

* cited by examiner

*Primary Examiner*—Kenneth R. Horlick
*Assistant Examiner*—Angela Bertagna
(74) *Attorney, Agent, or Firm*—Christensen O'Connor Johnson Kindness PLLC

(57) ABSTRACT

In one aspect, the present invention provides methods for synthesizing multiple copies of antisense cDNA molecules from an RNA molecule, comprising using an RNA molecule as a template for synthesizing multiple copies of antisense cDNA molecules. In some embodiments of the methods, the RNA molecule is incubated with a primer and with an enzyme possessing reverse transcriptase activity under suitable conditions for synthesizing multiple copies of antisense cDNA molecules. In some embodiments, the methods produce multiple copies of double-stranded cDNA from a template RNA molecule. In further embodiments, the methods produce multiple copies of cRNA from a template RNA molecule.

16 Claims, 2 Drawing Sheets

METHODS FOR RECYCLING MRNA FOR LINEAR CRNA AMPLIFICATION

CROSS-REFERENCE TO RELATED APPLICATION

This application claims the benefit of U.S. Provisional Application No. 60/437,246, filed Dec. 30, 2002.

FIELD OF THE INVENTION

The present invention relates to methods for preparing nucleic acid molecules from RNA template molecules.

BACKGROUND OF THE INVENTION

A DNA microarray allows the analysis of transcriptional expression of thousands of genes in a single assay (see, e.g., Ramsay (1998) *Nature Biotechnol.* 16:40–44; Marshall & Hodgson (1998) *Nature Biotechnol.* 16:27–31; Lashkari et al. (1997) *Proc. Natl. Acad. Sci.* (USA) 94:130–157; DeRisi et al. (1997) *Science* 278:680–6). The characterization of global cellular gene expression has many uses, including pathway dissection (see, e.g., Roberts et al. (2000) *Science* 287:873–80), classification of clinical samples (see, e.g., Khan et al. (1998) *Cancer Res.* 58:5009–13), drug evaluation (see, e.g., Hughes et al. (2000) *Cell* 102:190–26), and discovery of gene functions (see, e.g., Chu et al. (1998) *Science* 282:699–705).

In DNA microarray analyses, the identity of genes expressed in a sample and their levels of expression is determined by measuring the level of hybridization of nucleic acid "targets" to nucleic acid "probes" on the DNA microarray. A target sequence can be a messenger RNA (mRNA) present in the sample. More commonly, the target used is a nucleic acid molecule that is derived from the MRNA molecule and that has a sequence that is identical to, or complementary to, all, or a portion, of the mRNA molecule. A probe is a nucleic acid molecule on the DNA microarray that is complementary to a target.

Ideally, targets derived from MRNA molecules possess the following properties that facilitate their use in DNA microarray analyses. First, they should be representative of the mRNA population present in a sample. All, or substantially all, of the sequences in the mRNA population should be represented in the target sequence population used to screen the DNA microarray. Second, the relative abundance of each target sequence should be the same as the relative abundance of its corresponding mRNA in the sample. Third, each target should be present above a minimally detectable concentration to reliably measure its expression in the original samples. Fourth, the targets used to screen a DNA array should selectively hybridize to complementary nucleic acid molecules, and not hybridize to a significant extent to non-complementary nucleic acid molecules, immobilized on the DNA array or to the array surface surrounding the immobilized DNA.

The standard protocols for producing target RNA that can be used for DNA microarray analyses typically involves reverse transcribing RNA in a sample (starting RNA or input RNA) to generate double-stranded complementary DNA (cDNA), followed by an in vitro transcription reaction using the cDNA as a template to yield labeled complementary RNA (cRNA, also called antisense RNA). These protocols generally require microgram quantities of starting RNA to produce target cRNA for use in microarray analyses (Duggan et al. (1999) *Nat. Genet.* 21:10–14; Lockhart et al. (1996) *Nat. Biotechnol.* 14:1675–80; McGall et al. (1996) *Proc. Natl. Acad. Sci. U.S.A.* 93:13555–60; Schena et al. (1995) *Science* 270:467–70; Ramaswamy & Golub (2002) *J. Clin. Oncol.* 20:1932–1941). Thus, the applicability of these protocols is limited by the availability of sufficient quantities of starting RNA.

There are many situations in which either the total amount of RNA that can be obtained from a tissue sample is very low or in which there is a low copy number of expressed mRNA transcripts per cell. Thus, there is a need for methods for generating targets that can be used for microarray analyses from limited quantities of starting RNA.

SUMMARY OF THE INVENTION

In one aspect, the present invention provides methods for synthesizing multiple copies of antisense cDNA molecules from an RNA molecule, comprising using an RNA molecule as a template for synthesizing multiple copies of antisense cDNA molecules. In some embodiments of the methods, the RNA molecule is incubated with a primer and with an enzyme possessing reverse transcriptase activity under suitable conditions for synthesizing multiple copies of antisense cDNA molecules. A representative embodiment of the methods of this aspect of the invention comprises the steps of (a) incubating the RNA molecule with a primer and with an enzyme possessing reverse transcriptase activity under suitable conditions to synthesize a first antisense cDNA in a first RNA:DNA hybrid molecule; (b) denaturing the first RNA:DNA hybrid molecule; and (c) incubating the RNA molecule with a primer and with an enzyme possessing reverse transcriptase activity under suitable conditions to synthesize a second antisense cDNA molecule in a second RNA:DNA hybrid molecule. In some embodiments, more than two copies of antisense cDNA molecules are synthesized from the RNA molecule by repeating steps (b) and (c) with subsequent RNA-DNA hybrid molecules.

In some embodiments, the enzyme possessing reverse transcriptase activity lacks RNase H activity entirely or has an RNase H activity that can be reversibly activated and deactivated. The reverse transcriptase activity may be heat-stable, or stabilized using a stabilizing agent, such as trehalose. Alternatively, the reverse transcriptase activity may be periodically released from a stabilizing heat-sensitive matrix.

Another aspect of the invention provides methods for synthesizing multiple copies of double-stranded cDNA molecules from an RNA molecule. The methods of this aspect of the invention comprise the steps of (a) using an RNA molecule as a template for synthesizing multiple copies of antisense CDNA molecules; and (b) using the multiple copies of antisense cDNA molecules as templates for generating double-stranded cDNA molecules.

In a further aspect, the invention provides methods for generating linearly amplified RNA molecules from RNA template molecules. The methods of this aspect comprise the steps of (a) using an RNA molecule as a template for synthesizing multiple copies of antisense cDNA molecules; (b) using the multiple copies of antisense cDNA molecules as templates for generating double-stranded cDNA molecules; and (c) using the double-stranded cDNA molecules as templates for synthesizing amplified RNA. The amplified RNA can be used, for example, as targets in DNA microarray assays or other gene expression monitoring protocols.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as they would to one skilled in the art of the present invention.

In a first aspect, the present invention provides methods for synthesizing multiple copies of antisense cDNA molecules from an RNA molecule, comprising using an RNA molecule as a template for synthesizing multiple copies of antisense cDNA molecules. In some embodiments of the methods, the RNA molecule is incubated with a primer and with an enzyme possessing reverse transcriptase activity under suitable conditions to synthesize multiple copies of antisense cDNA molecules. A representative embodiment of the methods of this aspect of the invention comprises the steps of (a) incubating the RNA molecule with a primer and with an enzyme possessing reverse transcriptase activity under suitable conditions to synthesize a first RNA:DNA hybrid molecule; (b) denaturing the first RNA:DNA hybrid molecule; and (c) incubating the RNA molecule with a primer and with an enzyme possessing reverse transcriptase activity under suitable conditions to synthesize a second RNA:DNA hybrid molecule.

Preparation of RNA molecules useful as templates.

The methods of the invention use an RNA molecule as a template for synthesizing multiple copies of antisense cDNA molecules. RNA molecules useful as templates in the methods of this aspect of the invention can be isolated from any organism or part thereof, including organs, tissues, and/or individual cells. Suitably prepared crude cell lysates or permeabilized cells, either in solution or attached to a surface may be used (i.e., Laser Capture Microdissection samples affixed to plastic membranes or paraffin embedded cells). Any suitable RNA preparation can be utilized, such as total cellular RNA, or such as cytoplasmic RNA or such as an RNA preparation that is enriched for messenger RNA (mRNA), such as RNA preparations that include greater than 70%, or greater than 80%, or greater than 90%, or greater than 95%, or greater than 99% messenger RNA. Messenger RNA can be purified in accordance with any art-recognized method, such as by the use of oligo(dT) columns (see, e.g., Sambrook et al. (1989) *Molecular Cloning—A Laboratory Manual* (2d ed.), Vol. 1, Chapter 7, Cold Spring Harbor Laboratory, Cold Spring Harbor, N.Y.).

RNA may be isolated from eukaryotic cells by procedures that involve lysis of the cells and denaturation of the proteins contained therein. Cells of interest include wild-type cells, drug-exposed wild-type cells, modified cells, and drug-exposed modified cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al. (1979) *Biochemistry* 18:5294–5299). Messenger RNA is selected by selection with oligo-dT cellulose (see Sambrook et al. (1989) supra). Separation of RNA from DNA can also be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol. In some embodiments, samples are prepared by treatment with guanidine thiocyanate followed by capture, cleaning, and elution from a solid matrix (for example Qiagen RNEasy). This may be coupled with treatment of DNase to remove contaminating DNA.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. In other embodiments, the mRNA molecules of the RNA sample comprise at least 500, 1,000, 5,000, 10,000, 20,000, 30,000, 40,000, 50,000, 60,000, 70,000, 80,000 90,000 or 100,000 different nucleotide sequences. In another specific embodiment, the RNA sample is a mammalian RNA sample, the mRNA molecules of the mammalian RNA sample comprising about 20,000 to 30,000 different nucleotide sequences.

Priming the synthesis of antisense cDNA molecules.

In the first step of some embodiments of this aspect of the invention, the template RNA molecule is incubated with a primer that is suitable for priming the synthesis of an antisense cDNA molecule. The synthesis of antisense cDNA molecules is primed using any suitable primer, typically an oligonucleotide in the range of eight to 60 bases in length. The nucleic acid sequence of the oligonucleotide used to prime the synthesis of the antisense DNA molecules is therefore incorporated into the sequence of each synthesized antisense cDNA molecule. Oligonucleotides that are useful for priming the synthesis of antisense DNA molecules can anneal to any portion of the RNA template molecules, including the poly(A) tail.

In some embodiments, the synthesis of antisense cDNA molecules is primed using a first primer mixture comprising a multiplicity of first primers, wherein each of the first primers includes a random sequence portion and a defined sequence portion. The random sequence portion comprises a random sequence of nucleic acid residues. Statistically, it is likely that most, or all, of the random sequences are sufficiently complementary to a portion of one or more RNA template molecules, to be able to anneal thereto under the conditions utilized to anneal the first primer molecules to the RNA template molecules. The random sequence portion typically consists of from four to 20 nucleic acid residues, such as from four to 15 nucleic acid residues, such as from six to nine nucleic acid residues. In one embodiment, the random sequence portion consists of nine nucleic acid residues. Typically, the defined sequence portion is located 5' to the random sequence portion.

The defined sequence portion of the first primers comprises a known sequence of nucleic acid residues, and can include an RNA polymerase promoter. The RNA polymerase promoter sequence is therefore incorporated into the sequence of the antisense cDNA molecules, which can thereafter be used as templates for the synthesis of RNA molecules that are complementary in sequence to the antisense cDNA molecules. Any RNA polymerase promoter sequence can be included in the defined sequence portion of the first primers (for a description of naturally occurring RNA polymerase promoter or consensus promoter region, see Alberts et al. (1989) *Molecular Biology of the Cell* (2d ed.) Garland Publishing, Inc.). Representative examples of useful RNA polymerase promoters include a T7 RNA polymerase promoter and an SP6 RNA polymerase promoter. A representative defined sequence portion of a first primer that includes a T7 RNA polymerase promoter sequence is 5' ACTA TAG GGA GA 3' (SEQ ID NO: 1), which is the defined sequence portion of representative first primer molecule ShT7N9 5' ACTA TAG GGA GAN NNN NNN NN 3' (SEQ ID NO:2).

The nucleic acid sequence of an exemplary primer useful for priming the synthesis of an antisense cDNA molecule, and which does not include an RNA polymerase promoter sequence, is primer ShDNP256, which has the sequence 5' TAG ATG CTG TTG NNN NNN NNN 3' (SEQ ID NO:3). The defined sequence portion of ShDNP256 is 5' TAG ATG CTG TTG 3' (SEQ ID NO:4).

In some embodiments, the synthesis of the antisense cDNA molecules is primed using a mixture of primers, wherein the mixture includes oligo(dT) primers that each comprise an oligo(dT) portion and a defined sequence portion, wherein the oligo(dT) portion is located 3' to the defined sequence portion. The oligo(dT) portion of each oligo(dT) primer typically consists of from five to 25 nucleic acid residues, such as from 15–25 nucleic acid residues, such as 18 nucleic acid residues. In some embodiments, the oligo(dT) primers are used with a first primer mixture, wherein each of the first primers comprises a random sequence portion and a defined sequence portion. The nucleic acid sequence of the defined sequence portion of the oligo(dT) primer is typically identical to the nucleic acid sequence of the defined sequence portion of the primers of the first primer mixture. In this way, every antisense cDNA molecule includes the same defined sequence portion. Thus, in some embodiments, the defined sequence portion of the oligo(dT) primer comprises an RNA polymerase promoter, such as a T7 RNA polymerase promoter, such as the T7 RNA polymerase promoter having the nucleic acid sequence set forth in SEQ ID NO: 1. Another oligo(dT) primer useful in the methods of the invention is T7T18VN, which has the sequence 5' AAT TAA TAC GAC TCA CTA TAG GGA GAT TTT TTT TTT TTT TTT TTV N (SEQ ID NO:5).

Typically, for oligonucleotide primers less than 100 bases in length, annealing conditions are 50° to 10° C. below the homoduplex melting temperature ($T_m$); see generally, Sambrook et al. (1989) *Molecular Cloning: A Laboratory Manual*, 2nd ed., Cold Spring Harbor Press; Ausubel et al. (1987) *Current Protocols in Molecular Biology*, Greene Publishing).

Preparing oligonucleotides useful as primers.

The following remarks describe representative methods and compositions useful for making any oligonucleotide primer used in the practice of the present invention, including oligonucleotides useful for priming synthesis of antisense cDNA molecules.

A primer may be prepared by any suitable method, such as phosphotriester and phosphodiester methods of synthesis, or automated embodiments thereof. It is also possible to use a primer that has been isolated from a biological source, such as a restriction endonuclease digest.

An oligonucleotide primer can be DNA, RNA, PNA, chimeric mixtures, or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming the desired amplification reaction. An example of a possible modification is biotinylation, which may be used in combination with immobilized streptavidin as a means of purification.

For example, an oligonucleotide primer may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, and 2,6-diaminopurine.

In another embodiment, the oligonucleotide primer comprises at least one modified sugar moiety selected from the group including but not limited to arabinose, 2-fluoroarabinose, xylulose, and hexose.

In yet another embodiment, the oligonucleotide primer comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or analog thereof.

An oligonucleotide primer for use in the methods of the invention may be derived by cleavage of a larger nucleic acid fragment using non-specific nucleic acid cleaving chemicals or enzymes or site-specific restriction endonucleases; or by synthesis by standard methods known in the art, for example, by use of an automated DNA synthesizer (such as are commercially available from Biosearch, Applied Biosystems, etc.) and standard phosphoramidite chemistry. As examples, phosphorothioate oligonucleotides may be synthesized by the method of Stein et al. (1988) (*Nucl. Acids Res.* 16:3209–3221), methylphosphonate oligonucleotides can be prepared by use of controlled pore glass polymer supports (Sarin et al. (1988) *Proc. Natl. Acad. Sci. U.S.A.* 85:7448–7451).

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

Synthesis of a first antisense cDNA molecule.

In the practice of the invention, an RNA molecule is used as a template for synthesizing a first antisense cDNA molecule to form a first RNA:DNA hybrid. An antisense cDNA molecule can be complementary to a whole RNA template molecule, or to a portion thereof. For example, an antisense cDNA molecule can be complementary to the portion of a template RNA molecule that extends from the 3' end of the template RNA molecule to the midpoint of the template RNA molecule; similarly, by way of example, an antisense cDNA molecule can be complementary to the portion of an RNA template molecule that extends from the 5' end of the RNA molecule to the midpoint of the RNA molecule. Many antisense cDNA molecules are complementary to at least 50 contiguous bases of an RNA template molecule. In some embodiments, the complete complementary sequence of an RNA template molecule is represented in the population of antisense cDNA molecules; for example, the 5' half of the complementary sequence may be represented on one antisense cDNA molecule, and the 3' half of the complementary sequence may be represented on another antisense cDNA molecule.

Thus, a population of first antisense cDNA molecules is synthesized that includes individual first antisense cDNA molecules that are each complementary to all, or to a portion, of a template RNA molecule. Of the template RNA molecules that are represented in the population of first antisense cDNA molecules, typically at least 95% (more typically at least 98%) of the complementary sequence of each represented template RNA molecule is present in the population of first antisense cDNA molecules.

The first antisense cDNA molecules are synthesized by an enzyme possessing reverse transcriptase (RT) activity under conditions that allow the preservation of the template RNA molecules. Any reverse transcriptase activity is suitable to synthesize the first antisense cDNA molecules, such as those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT). In some embodiments, the enzyme possessing reverse transcriptase used is a MMLV-RT with a single amino acid substitution that eliminates RNase H activity while leaving the polymerase activity intact (e.g., POWERSCRIPT RT, BD Biosciences Clontech Laboratories, Inc., Palo Alto, Calif.). This allows the reverse transcriptase to synthesize a higher percentage of full-length antisense cDNA molecules and the RNA molecules are preserved intact for use as templates in one or more subsequent rounds of antisense cDNA synthesis (see below). In some embodiments, the enzyme possessing reverse transcriptase has controllable RNase activity, such as an MMLV-RT enzyme where the RNase H activity can be activated and deactivated by temperature or reactions conditions (e.g., salt, pH, charge).

The reverse transcriptase molecule preferably is thermostable so that the first strand synthesis reaction can be conducted at as high a temperature as possible, while still permitting hybridization of the primer to the RNA template molecule.

The conditions suitable for synthesizing an antisense cDNA molecule by reverse transcription of an RNA molecule include the presence at appropriate temperatures and for sufficient lengths of time of effective amounts of a reverse transcriptase and effective amounts of other reagents, such as buffers, dithiothreitol, RNase inhibitors, and a deoxynucleotide triphosphate mixture. Typically, the RNA is denatured at a first temperature, for example at about 65° C. to about 75° C. for between about 2 minutes and about 10 minutes (e.g., at about 70° C. for about 5 minutes). This is followed by annealing of the primer to the RNA at a second temperature, for example between about room temperature (i.e., typically between about 18° C. and 25° C.) to about 45° C. for between about 2 minutes and about 10 minutes (e.g., at around room temperature for about 10 minutes), followed by synthesis of antisense cDNA at a third temperature, for example between about 30° C. and about 50° C. for between about 15 minutes to about 2 hours (e.g., at around 42° C. for about 2 hours). Exemplary conditions for the synthesis of an antisense cDNA molecule from an RNA molecule are provided in EXAMPLE 1.

Synthesis of more than one antisense cDNA molecule from an RNA template.

In the second step of this aspect of the invention, the first RNA:DNA hybrid molecule formed in the first step is denatured. In the third step, the same RNA molecule used in the first step is used as a template for synthesizing a second antisense cDNA molecule to form a second RNA:DNA hybrid. Typically, the same conditions that apply to the synthesis of a first antisense cDNA molecule from an RNA template molecule are applicable to the synthesis of the second antisense cDNA molecule from the same RNA template molecule.

The synthesis of the second antisense cDNA molecule is generally primed using the same primer used for the synthesis of the first antisense cDNA molecule. In some embodiments of the third step, a fresh aliquot of primer is annealed to the RNA template. Alternatively, sufficient primer is added in the first step to prime the synthesis of a second antisense cDNA strand in the third step.

In some embodiments, a fresh aliquot of reverse transcriptase activity is added in the third step to synthesize a second antisense cDNA molecule. Alternatively, a reverse transcriptase activity is added in the first step that is not inactivated during the denaturation treatment in the second step. An example of a reverse transcriptase activity that is not inactivated during the second step is a heat-stable reverse transcriptase activity.

It is also possible to stabilize the reverse transcriptase activity so that all or most of its activity remains intact after the denaturation step. One way to stabilize the reverse transcriptase activity is to add a stabilizing agent. Protein stabilizing agents include polyols, sugars, as well as amino acids and amino acid analogs. Some examples include erythritol, sorbitol, glycerol, fructose, trehalose, proline, β-alanine, taurine and glycine betaine. These agents are sometimes referred to as cosmotropic agents and are well known in the art. (see, e.g., Jeruzalmi & Steitz (1997) *J. Mol. Biol.* 274:748–56 ). In some embodiments, the protein stabilizing agent is trehalose. The concentration of such agents will vary depending upon the type of agent employed. For example, if trehalose is used as the stabilizing agent, the concentration of trehalose used is typically between about 0.4 M and about 1.0 M.

Another way to preserve the reverse transcriptase activity during the denaturing of the RNA:DNA hybrid is to encase it in a wax or plastic matrix that releases the reverse transcriptase activity after the denaturation step. Exemplary wax or plastic matrices that are suitable for encasing the reverse transcriptase activity are paraffin, beeswax or other polyolefin waxes, as well as synthetic plastic polymers.

In some embodiments, more than two copies of antisense cDNA molecules are synthesized from each RNA template molecule by repeating the second and third step of the representative method until the desired number of antisense cDNA molecules have been synthesized.

In a second aspect, the invention provides methods for synthesizing multiple copies of double-stranded cDNA molecules from an RNA molecule. The methods of this aspect of the invention comprise the steps of (a) using an RNA molecule as a template for synthesizing multiple copies of antisense cDNA molecules; and (b) using the multiple copies of antisense cDNA molecules as templates for generating double-stranded cDNA molecules.

The first three steps of the methods of the first aspect of the invention, described above, can be used to synthesize multiple copies of antisense cDNA molecules in the practice of the first step of the second aspect of the invention. Thus, a template RNA molecule is incubated with a primer and an enzyme possessing reverse transcriptase activity under suitable conditions for synthesizing a first antisense cDNA molecule in a first RNA:DNA hybrid molecule, the first RNA:DNA hybrid molecule is denatured, and the template RNA molecules are incubated with a primer and an enzyme possessing reverse transcriptase activity under suitable conditions for synthesizing a second antisense cDNA molecule in a second RNA:DNA hybrid molecule, as described above for the first aspect of the invention. Additional copies of antisense cDNA molecules can be synthesized from the same RNA template by repeatedly denaturing the RNA:DNA hybrids formed and re-using the RNA as a template for the synthesis of one or more additional antisense cDNA molecules.

In the second step of this aspect of the invention, the copies of antisense cDNA molecules synthesized in the first step are used as templates for the synthesis of sense cDNA molecules that are complementary to the antisense cDNA to yield double-stranded cDNA molecules. Prior to, or concomitant with, the synthesis of sense cDNA molecules, the template RNA molecules are typically degraded or hydrolyzed. The RNA molecules may be degraded, for example, by adding an enzyme with RNase H activity. The RNA molecule may also be degraded by the RT enzyme if it has RNase H activity. Hydrolysis of the RNA template can be achieved, for example, by alkalinization of the solution containing the RNA template (e.g., by addition of an aliquot of a concentrated sodium hydroxide solution).

In some embodiments, all, or substantially all (typically more than 99%), of the primers used to prime the synthesis the antisense cDNA molecules are removed before synthesis of the sense cDNA molecules. The primers can be removed, for example, by applying the solution containing the RNA template molecules, antisense cDNA molecules, and primers, to a column that separates nucleic acid molecules on the basis of size or nucleic acid identity (RNA or DNA). The purified, antisense cDNA molecules, can then, for example, be precipitated and redissolved in a suitable buffer for the synthesis or the sense cDNA molecules.

The synthesis of sense cDNA molecules is primed using any suitable primer, typically an oligonucleotide in the range of ten to 60 bases in length, as described for the synthesis of antisense cDNA molecules. The nucleic acid sequence of the oligonucleotide used to prime the synthesis of the sense DNA molecules is therefore incorporated into the sequence of each synthesized sense cDNA molecule. Oligonucleotides that are useful for priming the synthesis of sense DNA molecules can anneal to any portion of the antisense cDNA template molecules.

In some embodiments, the primers used for synthesis of the sense cDNA molecules include a random sequence portion and a defined sequence portion, as describe above for the primers used to prime the synthesis of the antisense cDNA molecules. Typically, the primers used to prime the synthesis of the sense cDNA molecules do not have the same defined sequence portion as the primers used to prime the synthesis of the antisense cDNA molecules. In this way, both the antisense and the sense cDNA molecules include a unique defined primer sequence. The defined primer sequence included in the antisense cDNA molecules is not included in the sense cDNA molecules, and the defined primer sequence that is included in the sense cDNA molecules is not included in the antisense cDNA molecules. Depending on the choice of primer sequence, these defined primer sequences can be used, for example, to selectively direct DNA-dependent RNA synthesis from either the antisense or the sense cDNA molecules or, for example, to selectively direct DNA-dependent DNA synthesis from either the antisense cDNA molecules, or from the sense cDNA molecules.

Thus, in one representative embodiment of the methods of the invention, the defined sequence portion of the primers used to prime the synthesis of antisense cDNA molecules, includes, for example, the T7 RNA polymerase promoter sequence set forth in SEQ ID NO: 1, and the defined sequence portion of the primers used to prime the synthesis of the sense cDNA molecules does not include the T7 RNA polymerase promoter sequence (it may however, include a different RNA polymerase promoter sequence). Again, by way of representative example, in one embodiment of the methods of the invention, the defined sequence portion of the primers used to prime the synthesis of sense cDNA molecules includes, for example, the T7 RNA polymerase promoter sequence set forth in SEQ ID NO: 1, and the defined sequence portion of the primers used to prime the synthesis of the antisense cDNA molecules does not include the T7 RNA polymerase promoter sequence (it may however, include a different RNA polymerase promoter sequence). A representative nucleic acid sequence of a primer molecule, called ShT7N9, that includes a defined sequence portion including a T7 promoter sequence is set forth in SEQ ID NO: 2. An example of a primer that does not include an RNA polymerase promoter sequence is set forth in SEQ ID NO: 3, which shows the nucleic acid sequence of primer ShDNP256.

Oligonucleotides useful for priming synthesis of the sense cDNA molecules can be made using any art-recognized method, as described above with the oligonucleotides useful for the synthesis of the antisense cDNA molecules.

The priming for the sense cDNA molecules can also occur from the RNA fragments that are left behind after the RNase H activity hydrolyzes at least a portion of an RNA:DNA hybrid (Meyers et al. (1980) *Proc. Natl. Acad. Sci. U.S.A.* 77:1316; Olsen & Watson (1980) *Biophys. Res. Comm.* 97:1376), by self-priming by a hairpin loop formed at the 3' terminus of the antisense cDNA molecules (see, e.g., Efstratiadis et al. (1976) *Cell* 7:279), and non-specific priming by other DNA molecules in the reaction.

Thus, in the second step of the methods of this aspect of the invention, the antisense cDNA molecules are used as templates to synthesize sense cDNA molecules to form double-stranded cDNA molecules. A sense cDNA molecule can be complementary to a whole antisense cDNA molecule, or to a portion thereof. For example, a sense cDNA molecule can be complementary to a portion of an antisense cDNA molecule that is located between the 3' end of the antisense cDNA molecule and the midpoint of the antisense cDNA molecule; similarly, by way of example, a sense cDNA molecule can be complementary to a portion of an antisense cDNA molecule that is located between the 5' end of the antisense cDNA molecule and the midpoint of the antisense cDNA molecule. Typically, sense cDNA molecules are each complementary to at least 50 contiguous bases of an antisense cDNA molecule.

Thus, a population of sense cDNA molecules is synthesized that includes individual second DNA molecules that are each complementary to all, or to a portion, of a first DNA molecule. Typically, at least a portion of the complementary sequence of at least 95% (more typically at least 98%, such as at least 99%) of the antisense cDNA molecules are represented in the population of sense cDNA molecules. Of the antisense cDNA molecule complementary sequences that are represented in the population of sense cDNA molecules, typically at least 95% (more typically at least 98%, such as at least 99%) of the complementary sequence of each represented antisense cDNA molecule is present in the population of sense cDNA molecules.

The sense cDNA molecules are typically synthesized by an enzyme with DNA polymerase activity. In some embodiments, the sense cDNA molecules are synthesized by an enzyme having reverse transcriptase activity as well as DNA polymerase activity, such as the MMLV-RT. The enzyme may also have RNase H activity to degrade the RNA. Thus, an enzyme such as an MMLV reverse transcriptase having RNase H activity is suitable for synthesizing sense cDNA molecules. The MMLV-RT has three activities: RT, RNase H, and DNA polymerase. It is also possible to use a mixture of enzymes having reverse transcriptase activity, in which some of the enzymes also have RNase H activity. It may be more efficient to use a distinct enzyme for each activity, rather than one enzyme that possesses all activities.

In some embodiments, a DNA-dependent DNA polymerase is utilized to synthesize the sense cDNA molecules. For example, the Klenow fragment of DNA polymerase I can be utilized to synthesize the sense cDNA molecules.

Suitable conditions for synthesizing sense cDNA molecules using antisense cDNA molecules as templates include the presence at appropriate temperatures and for sufficient lengths of time of effective amounts of a DNA polymerase and other reagents, such as buffers and a deoxynucleotide triphosphate mixture. Typically, the antisense cDNA molecules is annealed to the primer at a first temperature (e.g., at around 70° C. for about 5 minutes), followed by elongation of an antisense cDNA molecules at a secondary temperature (e.g., at around 37° C. for about 60 minutes). Conditions for the synthesis of a sense cDNA molecule using antisense cDNA molecule as a template are well known in the art. Exemplary conditions for generating double-stranded cDNA from sense cDNA are provided in EXAMPLE 1.

In a third aspect, the invention provides methods for generating linearly amplified RNA molecules from a RNA template molecules. The methods of this aspect comprise the steps of (a) using an RNA molecule as a template for synthesizing multiple copies of antisense cDNA molecules; (b) using the multiple copies of antisense cDNA molecules as templates for generating double-stranded cDNA molecules; and (c) using the double-stranded cDNA molecules as templates for synthesizing amplified RNA.

The first two steps of the methods of the second aspect of the invention can be used to generate the double-stranded cDNA molecules in the practice of the third aspect of the invention. Thus, in the first step, an RNA template molecule is incubated with a primer and an enzyme with reverse transcriptase activity under suitable conditions for synthesizing multiple copies of antisense cDNA molecules, as described. In the second step, the antisense cDNA molecules are incubated with primer(s) and an enzyme with DNA polymerase activity under conditions suitable for synthesizing sense cDNA molecules to generate double-stranded cDNA molecules, as described above. Typically, either the primer used to synthesize the antisense cDNA strand or the primer used to synthesize the sense cDNA strand includes an RNA polymerase promoter sequence, which is then incorporated into either the antisense or the sense cDNA strand, respectively.

In the third step, the double-stranded cDNA is incubated with an enzyme possessing RNA polymerase activity and binding to the RNA polymerase promoter sequence incorporated into either the antisense or the sense cDNA strand under suitable conditions to synthesize RNA. If the primers used to synthesize the antisense cDNA molecules comprises an RNA polymerase promoter, amplified antisense RNA may be synthesized using the sense cDNA strand as a template (see, e.g., EXAMPLE 1). If the second defined nucleic acid sequence comprises an RNA polymerase promoter, amplified sense RNA may be synthesized using the antisense cDNA strand as a template. Successive rounds of transcription from either cDNA template results in amplified RNA.

The conditions suitable for synthesizing RNA using double-stranded cDNA molecules as templates include the presence at an appropriate temperature (e.g., around 37–42° C.) and for a sufficient length of time (e.g., for about 2–48 hours) of effective amounts of an RNA polymerase and other reagents, such as buffers, RNase inhibitors, dithiothreitol, and ribonucleotides (e.g., biotin-labeled ribonucleotides). Representative examples of useful RNA polymerase molecules include the SP6 RNA polymerase and the T7 RNA polymerase. Methods for in vitro transcription are well known to those of skill in the art (see, e.g., Van Gelder et al. (1990) *Proc. Natl. Acad. Sci. U.S.A.* 87:1663–1667; Eberwine et al. (1992) *Proc. Natl. Acad. Sci. U.S.A.* 89:3010–14). In some embodiments, the in vitro transcription reaction may be coupled with labeling of the resulting RNA.

Optionally, the RNA molecules can be labeled to facilitate the detection of the RNA molecules, for example when the labeled RNA molecules are used as targets in microarray analyses. The RNA molecules may be labeled with an amino-allyl-modified nucleotide (aa-UTP), as shown in EXAMPLE 1. Any amine-reactive suitable dye molecules can be used, provided that they are attached to the amplified RNA molecules by aminoallyl linkages. Examples of suitable dyes include fluorophores and chemiluminescers. Other dyes can be attached without incorporating a modified nucleotide, but using direct labeling methods (Kreatech ULS reagent). It is also possible to have a modified nucleotide, like biotin, that could react with a streptavidin enzyme, like horseradish peroxidase or alkaline peroxidase, which can in turn be used for chemiluminescent or colorimetric detection.

By way of example, amplified RNA molecules can be coupled to dye molecules via aminoallyl linkages by incorporating allylamine-derivatized ribonucleotides (e.g., allylamine-ATP, allylamine-CTP, allylamine-GTP, and/or allylamine-UTP) into the RNA molecules during synthesis of the RNA molecules. The allylamine-derivatized ribonucleotide(s) can then be coupled, via an aminoallyl linkage, to N-hydroxysuccinimide ester derivatives (NHS derivatives) of dyes (e.g., Cy-NHS, Cy3-NHS and/or Cy5-NHS). Again by way of example, in another embodiment, dye-labeled nucleotides may be incorporated into the RNA molecules during synthesis of the RNA molecules, which labels the RNA molecules directly.

It is also possible to include a spacer (usually 5–16 carbon atoms long) between the dye and the ribonucleotide, which may improve enzymatic incorporation of the modified nucleotides during synthesis of the RNA molecules. Representative examples of useful modified nucleotides and chemistries to combine dyes to them are provided in Hermanson, *Bioconjugate Techniques* (Academic Press, 1996).

An exemplary method for in vitro transcription and labeling of RNA is provided in EXAMPLE 1.

The RNA provided by the methods of this aspect of the invention may be used, for example, as a hybridization target in microarray assays. Before hybridization, the RNA may be fragmented. Methods for using RNA for hybridizing microarray assays are well known in the art. An exemplary method is provided in EXAMPLE 1.

EXAMPLE 1 describes an exemplary method of the invention for linearly amplifying cRNA. Using the methods of the invention (Recycling RT), it is possible to consistently produce over 20 micrograms of amplified RNA from 2 micrograms of total RNA from a variety of tissues, as shown in Table 2 in EXAMPLE 2. The methods of the invention provide at least as much amplified RNA from 2 micrograms of starting template RNA as an identical method using 5 micrograms of starting template RNA in which a single antisense cDNA is synthesized from each RNA template molecule (Standard RT), as shown in Table 1 and described in EXAMPLE 1. The amplified RNA produced according to the methods of the invention yield DNA microarray data that are as reproducible as the data obtained using amplified RNA produced according to the standard RT protocol, as shown in FIG. 1 and EXAMPLE 1. Thus, microarray analyses with targets produced using the methods of the invention are at least as reproducible as with targets produced using a standard RT protocol.

The following examples merely illustrate the best mode now contemplated for practicing the invention, but should not be construed to limit the invention.

EXAMPLE 1

This Example describes a comparison of microarray analyses results obtained using cRNA targets obtained using an exemplary linear amplification method of the invention (Recycling RT) and cRNA targets obtained using a standard RT protocol (Standard RT).

Two common samples were independently amplified in parallel using either the standard RT protocol or an exemplary method of the invention (Recycling RT). The standard RT protocol used was as described in Hughes et al. (2001) *Nat. Biotechnology* 19:342–34 (see also U.S. Pat. No. 6,132,997), with either 2 micrograms or 5 micrograms input total RNA. The Recycling RT protocol was as described below, using 2 micrograms input total RNA and two rounds of RT.

1. Synthesis of First Antisense cDNA Molecules.

Two micrograms of suitably prepared total RNA and 20 pmoles of T7T18VN primer were dehydrated in a 96 well half skirt plate. The sample plate was then resuspended in 10 microliters of RNase-free water for 15 minutes at room temperature followed by 15 seconds of plate vortexing. The primer was annealed to the mRNA target transcripts by incubating in a thermocycler at 65° C. for 10 minutes followed by 4° C. for 5 minutes.

To each sample well in the sample plate, 25 microliters of RT cocktail containing 8 microliters of 5X RT buffer (250 mM Tris-HCl, 15 mM $MgCl_2$, 375 mM KCl), 2 microliters of 10 mM dNTP's, 4 microliters of 50 mM $MgCl_2$, 6 microliters of RNase-free water, 4 microliters of DTT (100 mM), and 1 microliter Super-Script II RT was added. After addition of the RT cocktail to the sample wells, the plate is then incubated in a thermocycler for 2 hours at 42° C. followed by a quick cool to 4° C. At this point the RNA:DNA hybrid was denatured and the remaining primer was re-annealed to the mRNA by incubating in a thermocycler for 90° C. for 2 minutes, 4° C. for 5 minutes, 60° C. for 5 minutes, 4° C. hold.

2. Synthesis of Second Antisense cDNA Molecules and Sense cDNA Molecules.

Upon removal from the thermocycler, 3 microliters of MMLV RT was added to each sample well. After addition of MMLV RT to the sample wells, the plate was incubated in a thermocycler for 2 hours at 40° C., 65° C. for 15 minutes, 4° C. for 5 minute followed by a hold program at 25° C.

3. Synthesis of cRNA.

To each sample well in the sample plate, 60 microliters of IVT cocktail containing 22.8 microliters of RNase-free water, 16 microliters of 5X transcription buffer (0.2 M Tris-HCl (pH 7.5), 50 mM NaCl, 30 mM $MgCl_2$, and 10 mM spermidine), 8 microliters of 25 mM GTP, CTP, and ATP, 6 mM UTP, 3.3 microliters of 200 mM $MgCl_2$, 0.5 microliters of RNAguard, 2 microliters of 75 mM aa-UTP, 6 microliters of 100 mM DTT, 0.6 microliters of 2 kU/mL Inorganic Pyrophosphatase, and 0.8 microliters of 2.5 kU/microliter T7 Polymerase was added. Following the addition of IVT cocktail, the sample plate was incubated in a thermocycler for 16 hours at 40° C., 70° C. for 5 minutes, followed by a hold at 4° C.

4. Purification of cRNA.

Purification of the cRNA was carried using the Qiagen RNeasy purification platform. Samples were labeled with amino-allyl-UTP and coupled to Cy3 and Cy5 dyes. Table 1 shows a comparison of the yield of amino-allyl-cRNA using the Recycling RT protocol with 2 micrograms of input total RNA and the standard RT protocol with 2 micrograms or 5 micrograms of input total RNA.

TABLE 1

Comparison Yield of amino-allyl-cRNA using Recycling RT and Standard RT

| Tissue | Input Total RNA (micrograms) | Amino-allyl-cRNA Yield (micrograms) | Standard Deviation | CV (%) |
|---|---|---|---|---|
| Recycling RT | 2 | 45.13 | 2.02 | 4.47 |
| Standard RT | 5 | 37.16 | 1.53 | 4.12 |
| Standard RT | 2 | 22.14 | 1.00 | 4.50 |

Samples were hybridized to an in situ synthesis microarray in opposite dye channels and repeated for the other dye channel pair. The hybridization protocol was as described in Hughes et al. (2001) *Nat. Biotechnology* 19:342–34, except that the hybridization volume was 2 ml and the samples were hybridized for 48 hours. Data was combined for the microarrays.

Figure 1A:
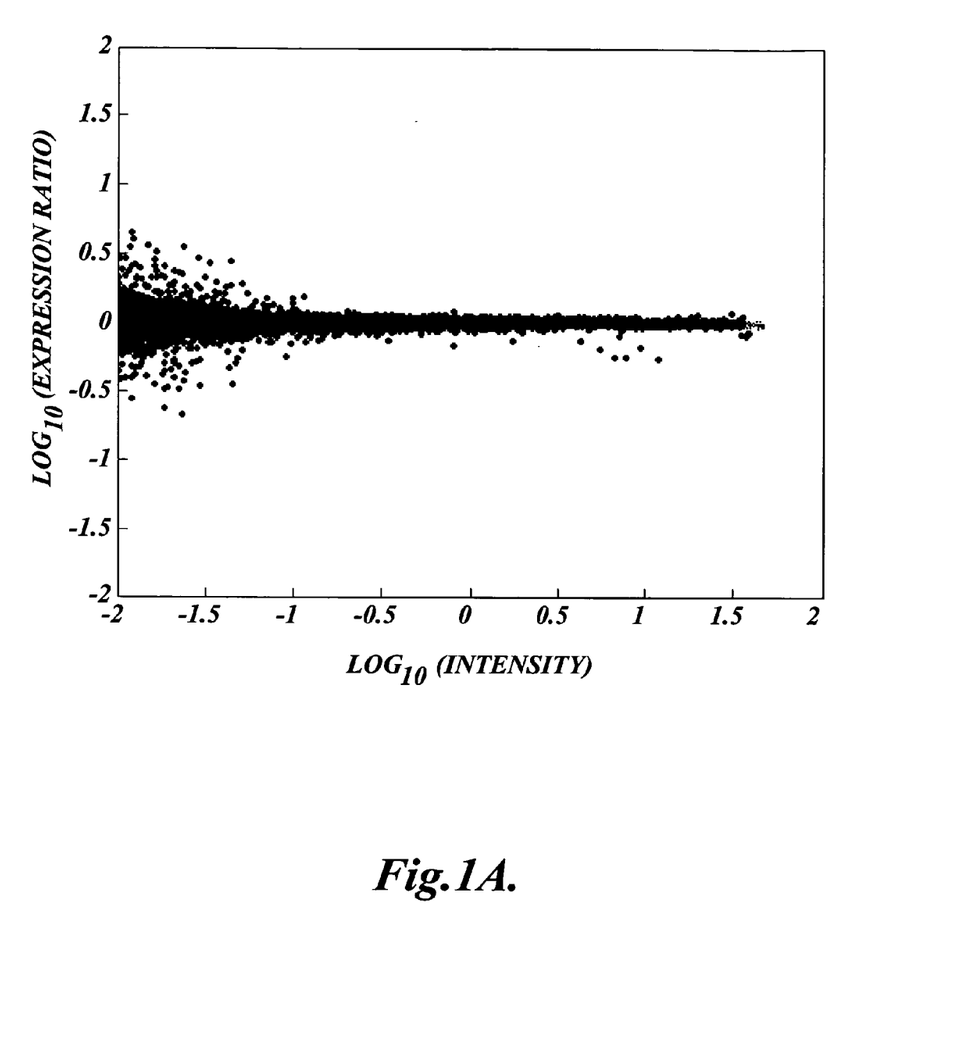
FIGS. 1A and 1B show two plots of the reproducibility of two independent amplifications obtained using a standard reverse transcription protocol (Standard RT) with 5 micrograms of starting total RNA (FIG. 1A) and using a representative method of the invention (Recycling RT) with 2 micrograms of starting total RNA (FIG. 1B), as described in EXAMPLE 1.
Figure 1B:
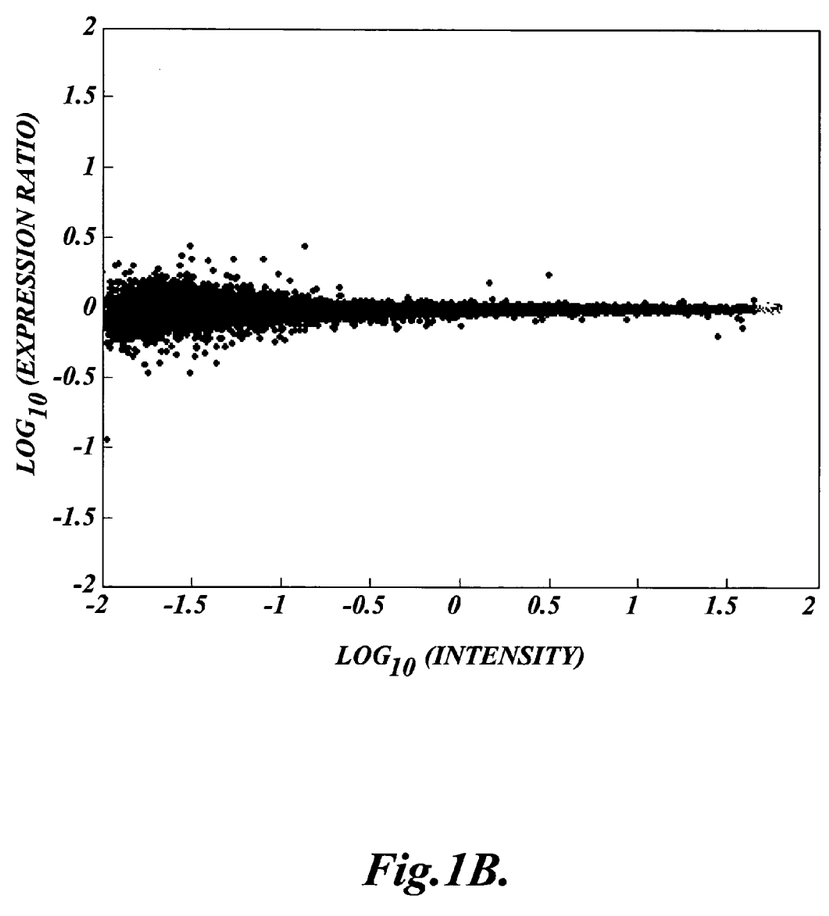

FIG. 1 compares the results using Standard RT with 5 micrograms of input total RNA (FIG. 1A) and Recycling RT with 2 micrograms of input total RNA (FIG. 1B). There are no significant false positives or skewing of the data using the Recycling RT protocol and the amplifications are highly reproducible (p-value<0.01).

EXAMPLE 2

This Example describes the yield of cRNA from input total RNA from various tissues using an exemplary method of the invention (Recycling RT) for linearly amplifying cRNA.

The Recycling RT protocol was as described in EXAMPLE 1, using 2 micrograms input total RNA and two rounds of RT. Table 2 shows the yield of amino-allyl-cRNA from 2 micrograms of input total RNA from brain, heart, testis, thymus, uterus, and spleen.

TABLE 2

Yield of amino-allyl-cRNA using Recycling RT

| Tissue | Amino-allyl-cRNA Yield (micrograms) | Standard Deviation | CV (%) |
| --- | --- | --- | --- |
| Brain | 32.35 | 0.66 | 2.03 |
| Heart | 19.65 | 1.19 | 6.06 |
| Testis | 29.11 | 0.17 | 0.58 |
| Thymus | 23.74 | 0.51 | 2.13 |
| Uterus | 26.70 | 1.08 | 4.06 |
| Spleen | 22.27 | 0.03 | 0.13 |

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A method for synthesizing multiple copies of antisense cDNA molecules from an RNA molecule, comprising:
   (a) incubating an RNA molecule with a primer and with an enzyme possessing reverse transcriptase activity under suitable conditions for synthesizing a first antisense cDNA molecule to yield a first RNA:DNA hybrid molecule;
   (b) denaturing the first RNA:DNA hybrid molecule at a temperature in the range of from 65° C. to 75° C.; and
   (c) incubating the RNA molecule with the primer and with the enzyme possessing reverse transcriptase activity under suitable conditions for synthesizing a second antisense cDNA molecule to yield a second RNA:DNA hybrid molecule.

2. The method of claim 1, wherein the enzyme possessing reverse transcriptase activity lacks RNAse H activity.

3. The method of claim 1, wherein the enzyme possessing reverse transcriptase activity is heat-stable.

4. The method of claim 1, wherein the enzyme possessing reverse transcriptase activity is periodically released from a heat-sensitive matrix.

5. The method of claim 1, wherein the reverse transcriptase activity is stabilized using a stabilizing agent.

6. The method of claim 5, wherein the stabilizing agent is trehalose.

7. The method of claim 1, wherein 2 antisense cDNA molecules are synthesized from the RNA molecule.

8. The method of claim 1, wherein 3 antisense cDNA molecules are synthesized from the RNA molecule.

9. A method for synthesizing multiple copies of double-stranded cDNA molecules from an RNA molecule, comprising:
   (a) using an RNA molecule as a template for synthesizing multiple copies of antisense cDNA molecules, wherein the method of synthesis includes incubating an RNA:DNA hybrid molecule at a temperature in the range of from 65° C. to 75° C.; and
   (b) using the multiple copies of antisense cDNA molecules as templates for generating double-stranded cDNA molecules.

10. A method for linearly amplifying complementary RNA molecules from an RNA molecule, comprising:
    (a) using an RNA molecule as a template for synthesizing multiple copies of antisense cDNA molecules, wherein the method of synthesis includes incubating an RNA:DNA hybrid molecule at a temperature in the range of from 65° C. to 75° C.;
    (b) using the multiple copies of antisense cDNA molecules as templates for generating double-stranded cDNA molecules; and
    (c) using the double-stranded cDNA molecules as templates for synthesizing complementary RNA.

11. A method for synthesizing multiple copies of double-stranded cDNA molecules from an RNA molecule, comprising:
    (a) incubating the RNA molecule with a primer and with a first enzyme possessing reverse transcriptase activity that lacks RNAse H activity under suitable conditions for synthesizing a first RNA:DNA hybrid molecule;
    (b) denaturing the first RNA:DNA hybrid molecule at a temperature in the range of from 65° C. to 75° C.;
    (c) incubating the RNA molecule with the primer and with the enzyme possessing reverse transcriptase activity under suitable conditions for synthesizing a second antisense cDNA molecule to yield a second RNA:DNA hybrid molecule;
    (d) denaturing the second RNA:DNA hybrid molecules at a temperature of 90° C.; and
    (e) incubating the antisense cDNA molecules with a primer and a second enzyme possessing DNA polymerase activity under suitable conditions for synthesizing double-stranded cDNA molecules.

12. The method of claim 11, wherein steps (a) to (c) are repeated at least three times.

13. The method of claim 11, wherein the reverse transcriptase activity is stabilized using a stabilizing agent.

14. The method of claim 13, wherein the stabilizing agent is trehalose.

15. The method of claim 11, wherein the second enzyme possessing DNA polymerase activity also possesses reverse transcriptase activity and RNAse H activity.

16. The method of claim 11, wherein the second enzyme possessing DNA polymerase activity is MMLV-RT.

* * * * *

SEQUENCE LISTING

```
<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
actataggga ga                                                          12

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (13)..(21)
<223> OTHER INFORMATION: n is a, c, g, or t

<400> SEQUENCE: 2
actataggga gannnnnnnn n                                                 21

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (13)..(21)
<223> OTHER INFORMATION: n is a, c, g, or t

<400> SEQUENCE: 3
tagatgctgt tgnnnnnnnn n                                                 21

<210> SEQ ID NO 4
<211> LENGTH: 12
<212> TYPE: DNA
<213> ORGANISM: Artificial Sequence
<220> FEATURE:
```

```
-continued

<223> OTHER INFORMATION: Oligonucleotide Primer

<400> SEQUENCE: 4
tagatgctgt tg                                                           12

<210> SEQ ID NO 5
<211> LENGTH: 46
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (45)..(45)
<223> OTHER INFORMATION: v is a, g or c
<220> FEATURE:
<221> NAME/KEY: misc_feature
<222> LOCATION: (46)..(46)
<223> OTHER INFORMATION: n is a, c, g, or t

<400> SEQUENCE: 5
aattaatacg actcactata gggagatttt tttttttttt ttttvn                      46
```